(12) United States Patent  
Martiska et al.

(10) Patent No.: US 8,335,343 B2  
(45) Date of Patent: Dec. 18, 2012

(54) METHOD FOR CHARACTERIZING POWDER IN A ROTATING CYLINDRICAL CONTAINER BY IMAGE ANALYSIS

(75) Inventors: Gregory P. Martiska, Newtown, CT (US); Paula L. Martiska, Newtown, CT (US)

(73) Assignee: Mercury Scientific Inc, Newtown, CT (US)

( * ) Notice: Subject to any disclaimer, the term of this patent is extended or adjusted under 35 U.S.C. 154(b) by 742 days.

(21) Appl. No.: 12/511,675

(22) Filed: Jul. 29, 2009

(65) Prior Publication Data

US 2011/0026760 A1  Feb. 3, 2011

(51) Int. Cl.  
*G06K 9/00* (2006.01)

(52) U.S. Cl. .......................... 382/100; 348/127; 250/573

(58) Field of Classification Search .................. 382/141, 382/142, 100; 348/127; 250/573, 559.4, 250/559.46; 356/426–428  
See application file for complete search history.

(56) References Cited

U.S. PATENT DOCUMENTS

| | | | | |
|---|---|---|---|---|
| 4,121,103 | A * | 10/1978 | Calhoun | 250/343 |
| 5,847,294 | A | 12/1998 | Poole | |
| 5,959,222 | A | 9/1999 | Poole | |
| 6,158,293 | A | 12/2000 | Poole | |
| 6,275,603 | B1 * | 8/2001 | Cronshaw et al. | 382/142 |
| 8,067,722 | B2 * | 11/2011 | Akkerman et al. | 250/223 B |
| 2007/0264051 | A1 * | 11/2007 | Tanaka | 399/254 |
| 2010/0192523 | A1 * | 8/2010 | Stoeckel et al. | 53/503 |

OTHER PUBLICATIONS

Dr. Brian H. Kaye, "Sampling and Characterization Research: Developing Two Tools for Power Testing", Powder and Bulk Engineering, vol. 10, No. 2, Feb. 1996, pp. 44-54.  
M A S Quintanilla, J M Valverde, A Castellanos,"The transitional behavior of avalanches in cohesive granular materials",Journal of Statistical Mechanics: Theory and Experiment,Jul. 31, 2006,P07105.  
A. Alexander, B Chaudhuri, A Faqih,F Muzzio, C Davies, M S Tomassone,"Avalanching flow of cohesive powders",Powder Technology 164,2006, pp. 13-21.  
Revolution Powder Analyzer Sales Brochure 2007, Mercury Scientific Inc., 27 Glen Road, Sandy Hook, CT 06482, www,MercSci.com.

* cited by examiner

*Primary Examiner* — Bhavesh Mehta  
*Assistant Examiner* — Shefali Goradia

(57) ABSTRACT

A method is provided for characterizing powders and powder behavior in a rotating cylindrical container by image analysis techniques. Powder is placed in a generally cylindrical container with transparent ends. The container is then placed in front of an imaging device and illuminated with a light source so the device can capture images of the powder over time. The container is then rotated at various speeds and the camera captures images of the powder at fixed time intervals. Image analysis algorithms are then used to isolate the powder information in the images and this data is used to calculate several parameters of the powder including the potential energy of the powder, the curvature of the powder, and volume of the powder. From these calculations, the average potential energy level of the powder, the potential energy level at which the powder yields or avalanches, the change in the potential energy before and after an avalanche, the powder surface curvature, and powder volume can be determined as a function of container rotation speed.

8 Claims, 4 Drawing Sheets

METHOD FOR CHARACTERIZING POWDER IN A ROTATING CYLINDRICAL CONTAINER BY IMAGE ANALYSIS

CROSS-REFERENCE TO RELATED APPLICATIONS

Not Applicable

BACKGROUND OF THE INVENTION

1) Field of the Invention

This invention relates to a method for characterizing powder samples by calculating the energy level of and forces produced on a powder within a rotating sample container and how the powder reacts to these forces. The information produced by these measurements can determine how well a powder performs in various processes and equipment such as pharmaceutical tableting machines, pneumatics conveyors, container filling machines, drying systems, and catalyst towers.

2) Description of the Related Art

Many systems have been disclosed and produced that measure powder properties in rotating cylindrical containers. These systems use various sensing techniques to measure powder behavior including photo-arrays, torque sensors, load cells, and video cameras. All of these systems consist of placing powder in a cylindrical sample container and then rotating the container about its lengthwise axis. The behavior of the powder due to the rotation of the sample container is then measured.

A system for characterizing powder avalanche in a rotating drum is disclosed by B. H. Kaye in Powder and Bulk Engineering, February, 1996. In the disclosed system, a light beam is directed through a transparent, rotating drum containing a powder sample. As the drum rotates, the powder avalanches at periodic intervals. A photocell array positioned on the opposite side of the drum is blocked to a greater or lesser degree as the powder avalanches within the drum. The output of the photocell array represents powder avalanching within the drum. This system only provides information as to the time between avalanches and does not calculate the energy level of the powder or forces acting on the powder or the energy released by each avalanche.

Another system for characterizing powder avalanches is disclosed in U.S. Pat. No. 5,847,294. In the disclosed system, a torque sensor is used to sense avalanches as the sample drum is rotated. The torque sensor measures the moment produced by the powder as it moves from the center of the drum to a position that is off center. When the powder avalanches, it moves back toward the center of the drum, reducing the moment and thus the torque on the torque sensor. This system provides information as to the time between avalanches and an indicator of avalanche size but does not calculate the energy level of the powder or forces acting on the powder or the energy released by each avalanche.

Another system for characterizing powder avalanches is disclosed in U.S. Pat. No. 5,959,222. In the disclosed system, an energy beam scanner is mounted inside the rotating sample drum to detect movement of the sample powder. The output of the energy beam scanner represents powder avalanching within the drum. This system only provides information as to the time between avalanches and does not calculate the energy level of the powder or forces acting on the powder or the energy released by each avalanche.

Another system for characterizing powder is disclosed by Alexander, Chaudhuri, Faqih, Muzzio Davies, Tomassone, in Powder Technology, January 2006. In the disclosed system, a load cell is used to sense powder position as the sample drum is rotated. The load cell measures the moment produced by the powder as it moves from the center of the drum to a position that is off center. When the powder avalanches, it moves back toward the center of the drum reducing the moment and thus the load on the torque sensor. This has the same weakness as the system disclosed in U.S. Pat. No. 5,847,294.

Another system for characterizing powder in a rotating drum is disclosed by M A S Quintanilla, J M Valverde, A Castellanos in the Journal of Statistical Mechanics, July 2006. In the disclosed system, a video camera is used to measure powder properties as the sample drum is rotated. In this system, angle of the powder is extracted from the images of the powder. Avalanches are detected by change in angle of the powder. This system does not calculate the energy level of the powder or forces acting on the powder or the energy released by each avalanche.

A commercial system for characterizing powder in a rotating drum is disclosed by Mercury Scientific Inc. In the disclosed system, a video camera is used to measure powder properties as the sample drum is rotated. In this system, angle of the powder and height of the powder in the sample drum is extracted from the images of the powder. The height of the powder is multiplied by the volume of the powder to produce a power value for the powder as it moves in the drum. Avalanches are detected by a change in the power of the powder. This system does not calculate the energy level of the powder or forces acting on the powder or the energy released by each avalanche. Also, powder angles are generally not reliably calculated because powders in rotating drums produce curved surfaces which have no defined angle.

None of the disclosed systems calculate or estimate the actual potential energy level of the powder as it is repositioned by the rotation of the sample container. They also do not calculate the amount of energy required to produce an avalanche in the powder or the amount of energy loss produced by an avalanche. They also do not measure the dependence of the potential energy, avalanche size, or energy required to produce an avalanche on the rotation speed of the container. Nor do they measure the curvature of the powder surface or the dependence of the curvature on rotation speed.

BRIEF SUMMARY OF THE INVENTION

After working on the commercial instrument produced by Mercury Scientific Inc. for some years, the inventors of the present invention determined that calculating the potential energy level of the powder in the rotating container is required to fully characterize a powder as it responds to the forces acting on it. Once the potential energy level is calculated, then the energy required to start an avalanche in a powder and the energy loss resulting from an avalanche could also be calculated. In addition, the calculation of the curvature of the powder is also a beneficial for characterizing a powder's behavior.

The invention presents a method for calculating the potential energy of powders in a rotating cylindrical container by image analysis techniques and thus characterizing powder behavior. Powder is placed in a generally cylindrical container with transparent ends. The container is then placed in front of an imaging device and illuminated with a light source so the imaging device captures images of the powder over time. The container is then rotated at various speeds and the imaging device captures images of the powder at fixed time intervals.

Image analysis algorithms are then used to isolate the powder information in the images and this data is used to calculate several parameters of the powder including the potential energy of the powder, the curvature of the powder, and volume of the powder. From these calculations, the average potential energy level of the powder, the potential energy level at which the powder yields or avalanches, the change in the potential energy before and after an avalanche, the powder surface curvature, and powder volume can be determined as a function of container rotation speed.

These calculations are useful because they describe how the powder reacts to the various forces acting on it in the rotating drum. The average potential energy level and the changes in potential energy as the powder avalanches can be used to predict how the powder will respond in various powder feeding systems and processes. In addition, the potential energy level of a powder before an avalanche quantifies the amount of energy require to get the powder to flow or yield. This energy level can be expressed as energy per unit volume or pressure by dividing the energy level by the volume of the powder. This is extremely useful for designing powders for small containers and manual powder delivery systems. Until this invention, this information was not available to scientists and engineers working with powders.

DETAILED DESCRIPTION OF THE INVENTION

Figure 1:
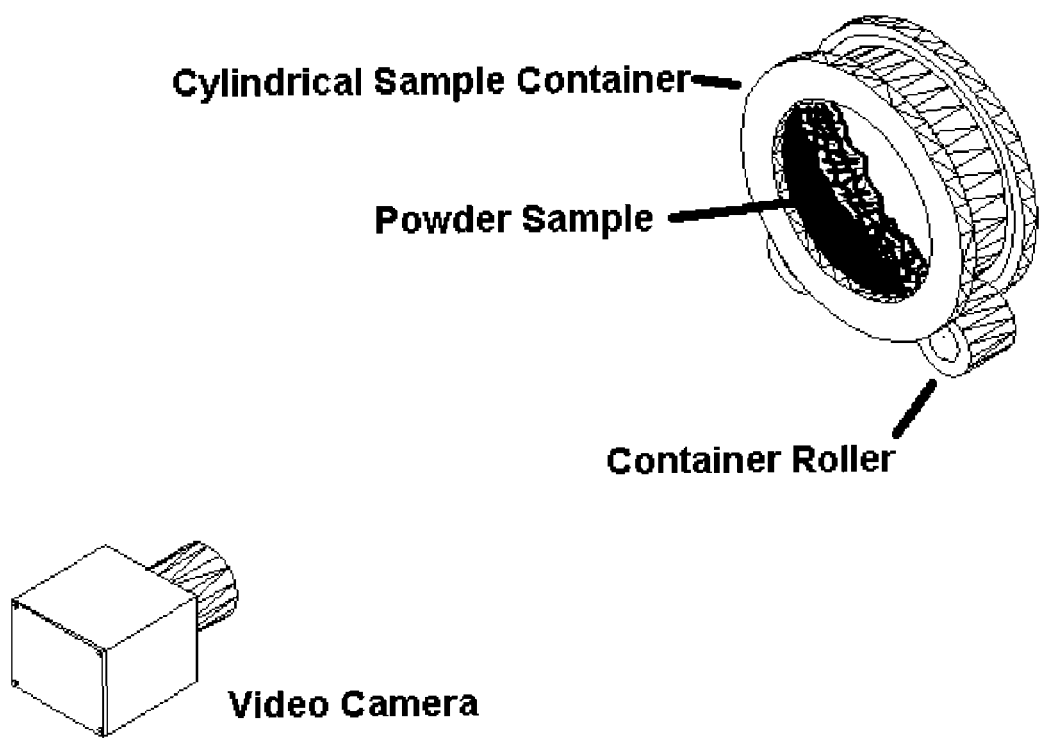
FIG. 1 presents a drawing of a typical system for collecting images of a powder in a rotating container.

The invention consists of methods for analyzing images of powder in a rotating generally cylindrical container. These images are usually collected by an imaging device that is perpendicular to the axis of the rotating container. Front or back light illumination can be used to illuminate the powder or distinguish it from its background. A servo or stepping motor is usually used to rotate the powder container and the powder sample volume in the container is usually one hundred cubic centimeters. This setup is pictured in FIG. 1.

Figure 2:
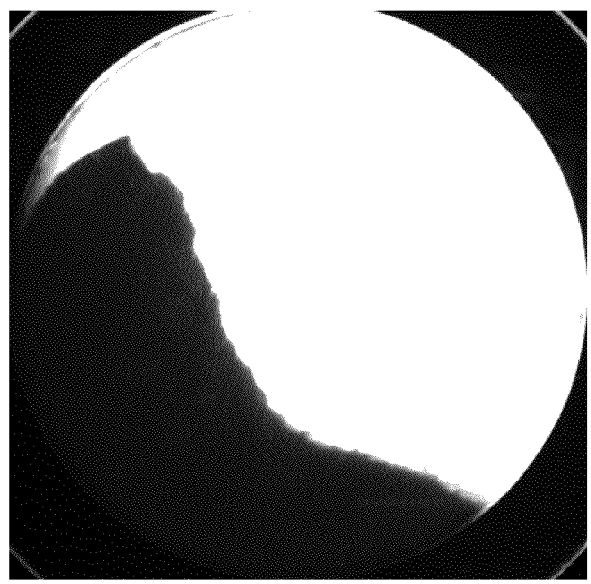
FIG. 2 presents an unprocessed digital image of the rotating sample container with powder.
Figure 3:
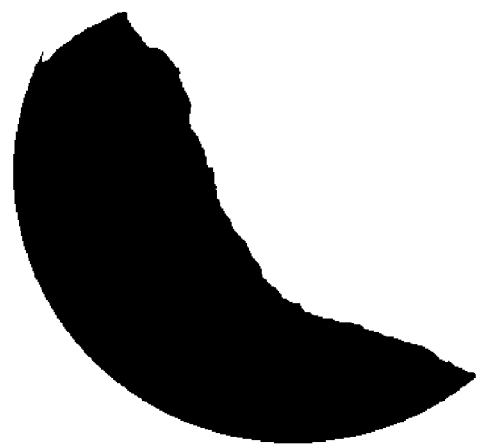
FIG. 3 presents the processed digital image isolating the powder from the sample container and background.

The images of the sample container are digitized and processed by standard image analysis techniques to identify pixels in the image that represent the sample powder. FIG. 2 displays a standard image of the sample container and FIG. 3 displays the image after it has been processed to isolate only the image of the powder.

The physical size represented by each pixel in the image is determined using the standard image analysis technique of taking an image of an object of known size. From the known size, the size represented by each pixel is calculated. In this case the normal size represented is in centimeters. The physical area represented by each pixel is also calculated and is usually expressed in square centimeters.

Figure 4:
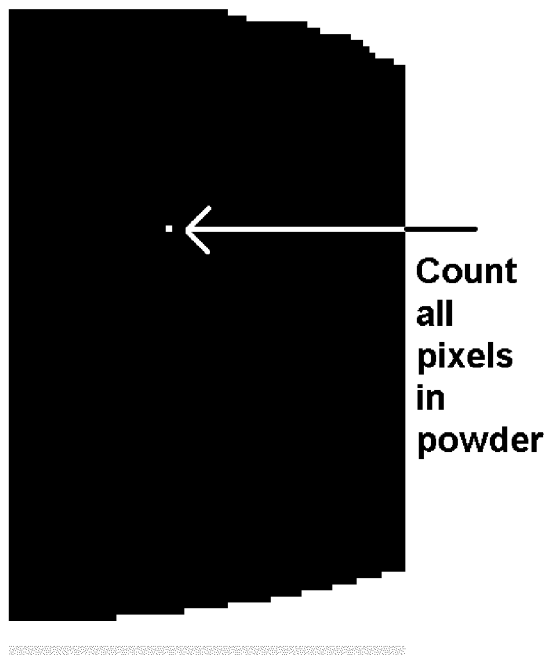
FIG. 4 presents the concept of adding all of the powder pixels to determine the volume of sample in the sample container. Only a slice of the powder is pictured.

The first step in calculating the potential energy of the powder is to measure the volume of the powder in the container. This can be done before the material is put in the container but preferably is calculated from the images of the powder themselves. The volume is calculated by adding up all of the pixels in the image that represent the powder and multiply this sum by the physical area represented by each pixel and the depth of the cylindrical container. FIG. 4 illustrates a pixel in the powder image. Calculating the volume for every image is preferable because it compensates for changes in the powder volume due to being mixed and aerated in the rotating sample container.

Figure 5:
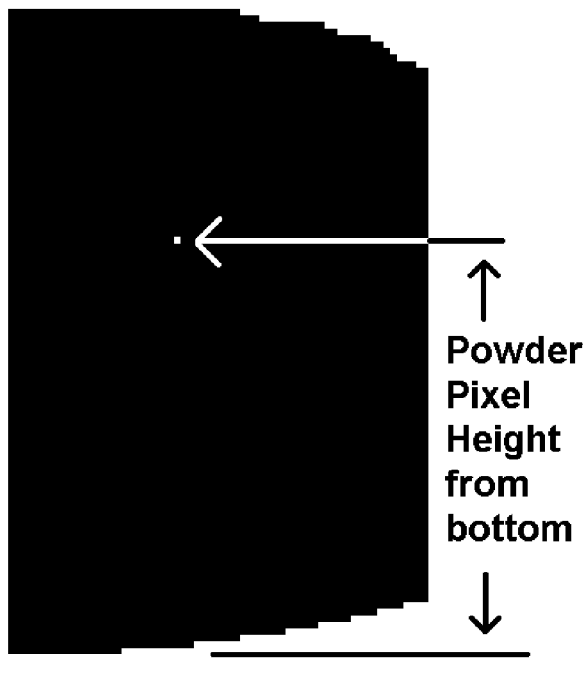
FIG. 5 presents the concept of adding the height of all of the powder pixels to determine the potential energy level of the powder. Only a slice of the powder is pictured.
Figure 6:
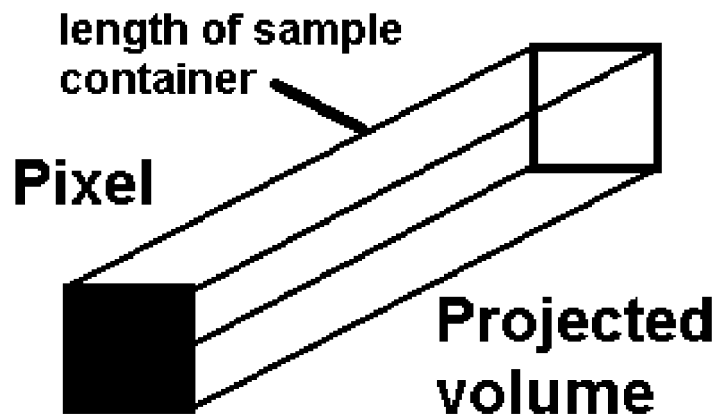
FIG. 6 presents the concept of the volume projection of a single pixel that is used to calculate the mass of powder represented by each pixel.

The next step is to add up the physical height from the bottom of the sample container of each pixel representing the powder. This physical height is determined by counting the number of vertical pixels from the bottom of the cylinder to the pixel of interest and multiplying by the physical size represented by each pixel in the image. FIG. 5 illustrates the height of a pixel in the powder image. This summation of the physical height of the powder pixels is converted to potential energy by multiplying it by the mass of powder represented by each pixel and by the force of gravity. The mass of powder represented by each pixel is determined by dividing the total mass of powder in the container by the volume of powder in the container and multiplying this value by the volume of powder represented by each pixel. The volume of powder represented by each pixel is calculated by multiplying the physical area represented by each pixel multiplied by the width of the cylindrical container. FIG. 6 illustrates the volume of powder represented by each pixel in the powder image. If the mass of the powder is in kilograms, the height of the powder is in meters and the force of gravity is in meters per second squared, the resulting potential energy units are in joules. This energy level can be expressed as energy per unit volume or pressure by dividing the energy level by the volume of the powder.

Figure 7:
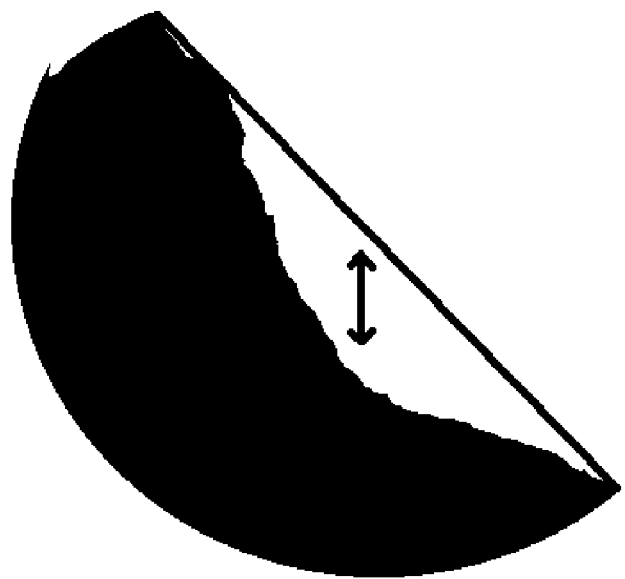
FIG. 7 presents the concept and analysis of curvature of the powder.

In addition to measuring the potential energy, the curvature of the powder surface is measured. This is achieved by determining the edge of the powder surface using image analysis techniques. This edge is represented by a series of points with the x coordinate being position in the sample container from left to right and the y coordinate being the height of the powder at the position represented by the x coordinate. The curvature of the powder surface is calculated from these points. There are several methods for calculating curvature. The preferred method is to calculate the line between the top pixel and bottom pixel of the powder image. The curvature can then be estimated by measuring the distance the powder surface is from the least squares line at the center of the powder surface. A negative value means the surface is concave and a positive value means the surface is convex. The size of the value indicates the degree of concavity or convexity. FIG. 7 illustrates the concept of curvature and the preferred method of its calculation.

After the potential energy levels and curvatures are calculated for all images of the powder, the next step is to analyze the data over time to find the local maxima and minima of the potential energy data. A local maximum in the potential energy value represent the point at which the powder avalanches and this values indicates the force required to cause an avalanche in the powder. The next local minima after each maximum represents the point at which the powder stops moving after the avalanche. The difference between the maximum and minimum pair represents the potential energy loss in the powder caused by the avalanche.

These values can be collected over long time intervals to produce average values for potential energy, energy required to produce an avalanche, and loss of energy on avalanche. Average curvature can also be calculated in this manner. The energy levels can be expressed as energy per unit volume or pressure by dividing the energy levels by the volume of the powder The next step is to measure the above parameters at various rotation speeds to determine the speed dependence of the measurements. This speed dependence can be expressed as the slope of the measurement versus speed as well as the standard deviations of the measurements versus speed.

What is claimed is:

1. A method for characterizing powder and granular material behavior in a rotating cylindrical container comprising:
   a) partially filling and closing a cylindrical container with transparent or semi-transparent ends with a known mass of a sample material consisting of a powder or granular material;
   b) orienting the cylindrical container so that it's length axis is in a horizontal position and then rotating it around its length axis at a known rotation speed causing the sample material to avalanche;
   c) acquiring a plurality of successive digital images of the sample material in the container using a camera with its optical axis within 45 degrees of the axis of rotation of the cylindrical container, a digital image being a matrix of pixels representing a two dimensional image of the sample material and cylindrical container with each pixel representing a physical height, physical width, and physical area of the sample material and cylindrical container;
   d) analyzing the digital images of the sample material and cylindrical container to determine a potential energy of the sample material in the cylindrical container for each image by :
      1) determining a pixel height for each pixel representing the sample material relative to the bottom side of the cylindrical container by counting the number of pixels in the vertical direction from the bottom side edge of the cylindrical container to each pixel representing the sample material and multiplying by a scale factor equal to the physical height each pixel represents in the image;
      2) calculating a pixel volume for the pixels making up the image by multiplying the length of the cylindrical container by a scale factor equal to the physical area each pixel represents in the image;
      3) calculating a total volume of the sample material in the cylindrical container by summing all of the pixels representing the sample material and multiplying by the pixel volume;
      4) calculating a pixel mass by multiplying the known mass of sample material in the cylindrical container by the the pixel volume and dividing by the total volume of the sample material in the cylindrical container;
      5) summing all of the pixel heights for each pixel representing the sample material multiplied by the pixel mass multiplied by standard gravity on the earth, otherwise known as the standard acceleration due to free fall and equal to approximately 9.8 meters per second squared.

2. A method for characterizing powder and granular material behavior in a rotating cylindrical container as described in claim 1 wherein a size of an avalanche of the sample material in the rotating cylindrical container is calculated by subtracting the potential energy of the sample material when an avalanche begins from the potential energy of the sample material when the avalanche ends, when an avalanche begins being a local maximum in the potential energy of the sample material in a plurality of successive images measured over time and when an avalanche ends being a minimum in the potential energy of the sample material in successive images after the local maximum.

3. A method for characterizing powder and granular material behavior in a rotating cylindrical container as described in claim 1 wherein a break energy of the sample material is determined by recording the potential energy of the sample material when an avalanche in the sample material begins, when an avalanche begins being a local maximum in the potential energy of the sample material in a plurality of successive images measured over time.

4. A method for characterizing powder and granular material behavior in a rotating cylindrical container as described in claim 1 wherein a break force required to start an avalanche in the sample material is determined by calculating the potential energy of the sample material when an avalanche in the sample material begins, when an avalanche begins being a local maximum in the potential energy of the sample material in a plurality of successive images measured over time, and dividing by the total volume of sample material in the cylindrical container.

5. A method for characterizing powder and granular material behavior in a rotating cylindrical container as described in claim 4 wherein the break force is measured at various rotation speeds to determine the rotational speed dependence of the break force.

6. A method for characterizing powder and granular material behavior in a rotating cylindrical container as described in claim 1 wherein the potential energy of the sample material and the total volume of the sample material are measured at various cylindrical container rotation speeds to determine the rotational speed dependence of the potential energy of the sample material and the total volume of the sample material.

7. A method for characterizing powder and granular material behavior in a rotating cylindrical container comprising:
   a) partially filling and closing a cylindrical container with transparent or semi-transparent ends with a known mass of a sample material consisting of a powder or granular material;
   b) orienting the cylindrical container so that it's length axis is in a horizontal position and then rotating it around its length axis at a known rotation speed causing the sample material to avalanche;
   c) acquiring a plurality of successive digital images of the sample material in the container using a camera with its optical axis within 45 degrees of the axis of rotation of the cylindrical container, a digital image being a matrix of pixels representing a two dimensional image of the sample material and cylindrical container with each pixel representing a physical height, physical width, and physical area of the sample material and cylindrical container;
   d) analyzing the digital images of the sample material to measure a curvature value for the top surface of the sample material, the curvature value being calculated in one of two methods:
      1) calculating the inverse of the radius of a circle whose perimeter best fits the top surface of the sample powder;
      2) adding the number of pixels from the top surface of the sample material in the center of the sample material to a surface line produced by connecting the highest point in the top surface of the sample material relative to the bottom side of the cylindrical container with the lowest point in the top surface of the sample material relative to the bottom side of the cylindrical container and multiplying by a scale factor equal to the physical height each pixel represents in the image and multiplying by negative one if the surface of the sample material is below the surface line.

8. A method for characterizing powder and granular material behavior in a rotating cylindrical container comprising as described in claim 7 wherein the curvature of the surface of the sample material is measured at various container rotation speeds to determine the rotation speed dependence of the curvature of the surface of the sample material.

* * * * *